United States Patent [19]

Lachhein

[11] Patent Number: 5,124,470
[45] Date of Patent: Jun. 23, 1992

[54] PROCESS FOR THE PREPARATION OF ARYLALKYLMETHYLSILANES

[75] Inventor: Stephen Lachhein, Hofheim am Taunus, Fed. Rep. of Germany

[73] Assignee: Hoechst Aktiengesellschaft, Frankfurt am Main, Fed. Rep. of Germany

[21] Appl. No.: 732,792

[22] Filed: Jul. 19, 1991

[30] Foreign Application Priority Data

Jul. 21, 1990 [DE] Fed. Rep. of Germany ....... 4023288

[51] Int. Cl.⁵ ................................ C07F 7/08
[52] U.S. Cl. .................................... 556/480
[58] Field of Search ......................... 556/480

[56] References Cited

U.S. PATENT DOCUMENTS

| | | | |
|---|---|---|---|
| 2,286,763 | 6/1942 | Rochow | 556/480 |
| 2,561,178 | 7/1951 | Burkhard | 556/480 X |
| 2,813,886 | 11/1957 | Ramsden | 556/480 |
| 2,813,887 | 11/1957 | Ramsden | 556/480 |
| 4,593,112 | 6/1986 | Takamizawa et al. | 556/480 |

Primary Examiner—Paul F. Shaver
Attorney, Agent, or Firm—Curtis, Morris & Safford

[57] ABSTRACT

The present invention relates to a process for the preparation of arylalkylmethylsilanes of the formula I

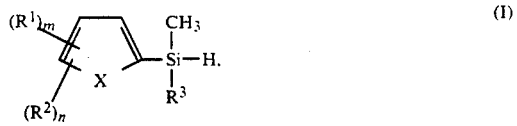

where X is CH=CH, N=CH, CH=N or S, $R^1$ and $R^2$ independently of one another are H, halogen, ($C_1$ to $C_4$)alkyl, ($C_1$ to $C_4$)alkoxy, ($C_1$ to $C_4$)alkylthio, ($C_1$ to $C_4$)haloalkyl, ($C_1$ to $C_4$)haloalkoxy or ($C_1$ to $C_4$)haloalkylthio, $R^3$ is ($C_1$ to $C_6$)alkyl and m and n are 0, 1 or 2, which comprises reacting dichloromethylsilane II

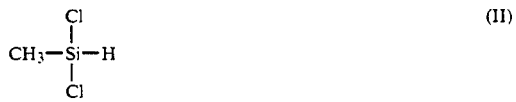

first with an arylmagnesium halide of the formula III

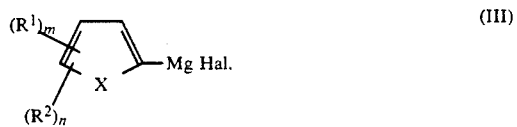

where $R^1$, $R^2$, m, n and X are as defined in Formula I and Hal is halogen, at temperatures of from −78° to 0° C., and subsequently with an alkylmagnesium halide of the formula IV $$R^3\text{—Mg Hal} \qquad (IV),$$

where $R^3$ is as defined in formula I and Hal is halogen, if appropriate in the presence of a solvent.

3 Claims, No Drawings

PROCESS FOR THE PREPARATION OF ARYLALKYLMETHYLSILANES

The present invention relates to a process for the preparation of arylalkylmethylsilanes of the formula I

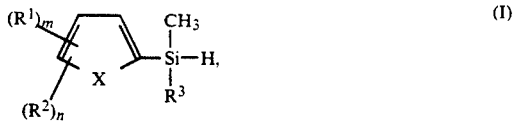

where
X is CH=CH, N=CH, CH=N or S,
$R^1$ and $R^2$ independently of one another are H, halogen, ($C_1$ to $C_4$)alkyl, ($C_1$ to $C_4$)alkoxy, ($C_1$ to $C_4$)alkylthio, ($C_1$ to $C_4$)haloalkyl, ($C_1$ to $C_4$)haloalkoxy or ($C_1$ to $C_4$)haloalkylthio,
$R^3$ is ($C_1$ to $C_6$)alkyl and
m and n are 0, 1 or 2,
which comprises reacting dichloromethylsilane II

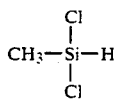

first with an arylmagnesium halide of the formula III

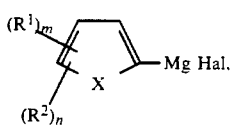

where $R^1$, $R^2$, m, n and X are as defined in formula I and Hal is halogen, at temperatures of from $-78°$ to $0°$ C., and subsequently with an alkylmagnesium halide of the formula IV

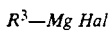

where $R^3$ is as defined in formula I and Hal is halogen, if appropriate in the presence of a solvent.

The sequence of the reaction of the dichloromethylsilane with the Grignard reagents III and IV is a characteristic feature of the process according to the invention. The reaction of the compound II with the compound III is preferably carried out at temperatures of from $-50°$ to $-10°$ C.

The compounds of the formulae I, III and IV are known and act as precursors for insecticidal, acaricidal or nematocidal active substances (EP-A 0,224,024, or the references cited under 1) to 7)).

It is known to synthesize the compounds I starting from chlorodimethylsilane, which is expensive and only available in limited quantities.

Alternatively, the arylalkylmethylsilanes I can be prepared by reducing corresponding halo- or alkoxysilanes, which causes problems when carried out on an industrial scale (EP 0,224,024).

The process according to the invention avoids both shortcomings. Particularly surprising was the fact that the monosubstitution product was formed with very high yields, since the selective formation of a monosubstitution product in a reaction of the compound of the formula II with one of the two Grignard reagents could not have been anticipated.

To achieve high yields and to avoid complicated removal of the initially desired monosubstitution product, it is essential that the reaction of the compound of the formula II is selective. The yields of monosubstitution product[1 to 6] of other of other dihalosilanes such as, for example, dichlorodimethylsilane, with an equivalent of Grignard reagent are only average. Moreover, the selective Grignardization of methyldichlorosilane II with an equivalent of Grignard reagent has not previously been described[1 to 6].

For achieving a sufficiently high selectivity at all, the Grignard reagents are therefore often employed in large excess, which is unfavorable from the economical and ecological point of view[1,2,6]. Another possibility of directing the reaction towards the monosubstitution products consists in first exchanging a halogen function for an amine radical, then reacting the product with the organometallic reagent and finally converting the resulting aminosilane into the desired chlorosilane[7]. Naturally, the suitability of this process for large-scale application is only limited because of the number of steps involved.

1) K. A. Adrianov, N. V. Delazari, Doklady Akad. Nauk. SSSR 122, 393. Engl. ed. p. 689;
2) R. N. Lewis, J. Amer. Chem. Soc. 70, 1115 (1948);
3) D. W. Lewis, G. C. Gainer, J. Amer. Chem. Soc. 74, 2931 (1952);
4) V. A. Ponomarenko, A. Snegova, Yu. P. Egorov, Izvest. Akad. Nauk. SSSR, Otdel Khim. Nauk 1960, 244; Engl. ed. p. 222;
5) L. W. Breed, W. J. Haggerty jr., J. Org. Chem. 27, 257 (1962);
6) J. Hetfleijs, F. Mares, V. Clevalovsky, Collection Czech. Chem. Commun. 30, 1643 (1965);
7) M. Takamizawa, M. Unemura (Shin-Etsu Chem. Industry Co., Ltd.), Jpn. Kokai Tokkyo Koko 79, 109, 923 (29.8.1979), Appl. 78/16063 (15.2.1978); C. A. 92, 146898 (1980);

However, when the reaction is controlled in a suitable fashion, the compound of the formula II (methyldichlorosilane) surprisingly reacts entirely selectively with an equivalent of Grignard reagent of the formula III to give the intermediates of the formula V a

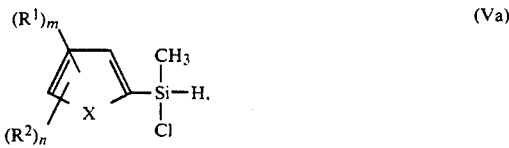

which are generally not isolated and which then, with an equivalent of Grignard reagent of the formula IV, subsequently give the compounds of the formula I. The yields in the process according to the invention are higher than 90% of theory. For the selective formation of the products I, it is essential to follow the sequence of the Grignard reactions of the process according to the invention. If the methyldichlorosilane II is first reacted with the Grignard reagent IV and then subsequently with the Grignard reagent III, then the selectivity and hence the yield of I is lowered drastically.

It was therefore surprising and unexpected that the reaction of the compound of the formula III with II proceeds with high yields of monosubstitution product, in contrast to the examples of the references.

Analogously to the examples of the references (see Comparison Example I), the monosubstitution product V b cannot be prepared in the desired yields and purities by reacting the compound II with the compound IV

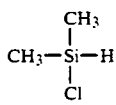

$$\begin{array}{c} CH_3 \\ | \\ CH_3-Si-H \\ | \\ Cl \end{array} \quad (IV)$$

It is furthermore necessary to carry out the first Grignard reaction to give the monosubstitution product V a in a temperature range between −78° and 0 ° C., preferably at −50° to −10° C., if it is intended to achieve a sufficiently high selectivity and yields of more than 90% of theory, the optimum temperature range varying as a function of the organic radical of the Grignard reagent III (see Comparison Example II). The replacement of the second halogen can then be effected at any desired temperature within an interval from −78° to 200 ° C., preferably 0° to 100 ° C. Solvents which are used are ether-type solvents such as, for example, diethyl ether, diisopropyl ether, dibutyl ether, tetrahydrofuran, glyme, diglyme, triglyme, tetraglyme or dioxane, and mixtures of these with aliphatic or aromatic hydrocarbons such as, for example, hexane, heptane, benzene, toluene or xylene. The preferred solvent is tetrahydrofuran. 1.00 to 1.50 mol, preferably 1.00 to 1.25 mol, of the Grignard reagent used for the first substitution are employed per mole of the compound of the formula II. The organometallic compound which is used for the second substitution is preferably used with 1.00 to 2.00 mol, preferably 1.00 to 1.50 mol, per mole of the compound of the formula II.

The reaction product (compound of the formula I) is worked up in a customary manner, for example by adding water, separating off the salt solution, and evaporating the organic phase. The crude product obtained is so pure that a simple thin-layer distillation is sufficient for further chemical reactions to be subsequently carried out with the product.

The process according to the invention is illustrated by the examples which follow:

Use examples:

Preparation of 4-ethoxyphenyldimethylsilane

A Grignard solution prepared from 481.4 g of 4-bromophenetole, 61.0 g of magnesium and 1820 ml of tetrahydrofuran is added dropwise at −40 ° C. to a solution of 316 g of dichloromethylsilane in 1450 ml of anhydrous tetrahydrofuran. Stirring is subsequently continued for 1 hour at −40 ° C., and the mixture is allowed to slowly warm to room temperature. After 1175 ml of a 3M methylmagnesium chloride solution in tetrahydrofuran have been added, the mixture is refluxed for 1 hour and cooled to 30 ° C., and the excess Grignard reagent is decomposed by the dropwise addition of 1100 ml of water. The phases are separated, and the aqueous phase is extracted using 500 ml of tetrahydrofuran. The combined organic phases are freed from solvent in vacuo, and the crude product is distilled in a thin-layer evaporator. 417 g of crude product of a purity of 94.3% (GC) are obtained, which corresponds to a yield of 91.1% of theory. The boiling point at 0.012 bar is 78° to 82 ° C.

Following this procedure, the following compounds, inter alia, are obtained in high yield and purity:

| | |
|---|---|
| 4-Ethoxyphenylethylmethylsilane | 92.0% yield |
| Purity 95.7%  B.p.$_{12}$ = 88 to 90° C. | |
| Phenylhexylmethylsilane | 90.4% yield |
| Purity 94.6%  B.p.$_{11}$ = 124 to 128° C. | |
| (2-Ethylthien-5-yl)dimethylsilane | 90.2% yield |
| Purity 93.4%  B.p.$_{12}$ = 90 to 94° C. | |
| (2-Ethylthiopyrid-5-yl)dimethylsilane | 91.0% yield |
| Purity 93.5%  B.p.$_{12}$ = 118 to 124° C. | |
| <2-(2,2,2-Trifluoroethoxy)pyrid-5-yl>-dimethylsilane | 90.8% yield |
| Purity 92.8%  B.p.$_{11}$ = 120 to 124° C. | |

COMPARISON EXAMPLE I 1175 ml of a 3M methylmagnesium chloride solution in tetrahydrofuran are slowly added dropwise at −40 ° C. to a solution of 316 g of dichloromethylsilane in 1450 ml of anhydrous tetrahydrofuran. Stirring is subsequently continued for 1 hour at −40 ° C., and the mixture is allowed to slowly warm to room temperature.

A Grignard solution which has been prepared from 481.4 g of 4-bromophenetole, 61.0 g of magnesium and 1820 ml of tetrahydrofuran is added, and the mixture is then refluxed for 1 hour and cooled to 30 ° C., and the excess Grignard reagent is decomposed by the dropwise addition of 1100 ml of water. The phases are separated and the aqueous phase is extracted using 500 ml of tetrahydrofuran.

The combined organic phases are freed from solvent in vacuo, and the crude product is distilled in a thin-layer evaporator. 234.6 g of product of a purity of 95.4% (GC) are obtained, which corresponds to a yield of 46.3% of theory. The boiling point at 0.012 bar is 78° to 82 ° C. Comparison Example II:

A Grignard solution prepared from 481.4 g of 4-bromophenetole, 61.0 g of magnesium and 1820 ml of THF is added dropwise at +10 ° C. to a solution of 316 g of dichloromethylsilane in 1450 ml of anhydrous THF. Stirring is subsequently continued for 1 hour at +10 ° C., and the mixture is allowed to slowly warm to room temperature.

After 1175 ml of 3M methylmagnesium chloride solution in THF have been added, the mixture is refluxed for 1 hour and cooled to 30° C., and the excess Grignard reagent is decomposed by the dropwise addition of 1100 ml of water. The aqueous salt solution is separated off, and the aqueous layer is washed with tetrahydrofuran.

The solvent is distilled off in vacuo, and the crude product is distilled in a thin-layer evaporator. 332 g of product of a purity of 93.2% are obtained, which corresponds to a yield of 64.9% of theory. The boiling point at 0.016 bar is 84° to 86 ° C.

I claim:

1. A process for the preparation of arylalkylmethylsilanes of the formula I

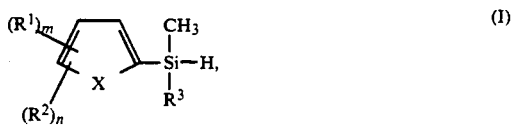

where

X is CH=CH, N=CH, CH=N or S, $R^1$ and $R^2$ independently of one another are H, halogen, ($C_1$ to $C_4$)alkyl, ($C_1$ to $C_4$)alkoxy, ($C_1$ to $C_4$)alkylthio, ($C_1$ to $C_4$)haloalkyl, ($C_1$ to $C_4$)haloalkoxy or ($C_1$ to $C_4$)haloalkylthio, $R^3$ is ($C_1$ to $C_6$)alkyl and m and n are 0, 1 or 2, which comprises reacting dichloromethylsilane II

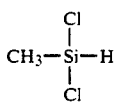

(II)

first with an arylmagnesium halide of the formula III

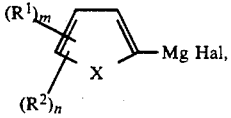

(III)

where $R^1$, $R^2$, m, n and X are as defined in formula I and Hal is halogen, at temperatures of from $-78°$ to $0°$ C., and subsequently with an alkylmagnesium halide of the formula IV $$R^3-Mg\ Hal \qquad (IV).$$

where $R^3$ is as defined in formula I and Hal is halogen, if appropriate in the presence of a solvent.

2. The process as claimed in claim 1, which comprises reacting the compound of the formula II with the compound of the formula III at temperatures of form $-50°$ to $-10°$ C.

3. The process as claimed in claim 1, which comprises using tetrahydrofuran as the solvent.

* * * * *